(12) United States Patent
Ray, II

(10) Patent No.: US 8,327,610 B1
(45) Date of Patent: Dec. 11, 2012

(54) CAPSULE OPENER AND EMPTIER

(75) Inventor: Jay Richard Ray, II, Conroe, TX (US)

(73) Assignee: JCDS Holdings, LLC, Conroe, TX (US)

( * ) Notice: Subject to any disclaimer, the term of this patent is extended or adjusted under 35 U.S.C. 154(b) by 0 days.

(21) Appl. No.: 13/564,391

(22) Filed: Aug. 1, 2012

Related U.S. Application Data

(63) Continuation of application No. 13/328,481, filed on Dec. 16, 2011, now abandoned.

(51) Int. Cl.
*B67B 7/00* (2006.01)

(52) U.S. Cl. .................. 53/492; 53/381.2; 128/203.21; 222/81

(58) Field of Classification Search .............. 53/435, 53/492, 513, 381.2; 128/203.21; 222/81, 222/85; 414/412; 604/411
See application file for complete search history.

(56) References Cited

U.S. PATENT DOCUMENTS

| | | | |
|---|---|---|---|
| 3,518,992 A | 7/1970 | Altounyan et al. | |
| 3,739,471 A * | 6/1973 | Peres ........................... | 414/412 |
| 3,971,377 A | 7/1976 | Damani | |
| 4,423,724 A * | 1/1984 | Young ....................... | 128/203.21 |
| 4,884,565 A | 12/1989 | Cocozza | |
| 4,995,385 A * | 2/1991 | Valentini et al. ......... | 128/203.21 |
| 5,070,870 A | 12/1991 | Pearce | |
| 5,263,475 A | 11/1993 | Altermatt et al. | |
| 5,370,268 A * | 12/1994 | Adams ......................... | 414/412 |
| 5,379,763 A * | 1/1995 | Martin ..................... | 128/203.21 |
| 5,522,383 A * | 6/1996 | Calvert et al. ............ | 128/203.21 |
| 5,562,918 A | 10/1996 | Stimpson | |
| 5,797,391 A | 8/1998 | Cook et al. | |
| 6,705,313 B2 | 3/2004 | Niccolai | |
| 7,284,553 B2 | 10/2007 | Hochrainer | |
| 7,559,325 B2 * | 7/2009 | Dunkley et al. .......... | 128/203.21 |
| 7,832,399 B2 | 11/2010 | Ganem et al. | |
| 2010/0300440 A1 | 12/2010 | Deboeck et al. | |

* cited by examiner

*Primary Examiner* — Stephen F Gerrity
(74) *Attorney, Agent, or Firm* — Akerman Senterfitt

(57) ABSTRACT

The present embodiments are directed to a medicinal extractor that may open and empty pharmaceutical capsules of variable sizes. The medicinal extractor may have a cover that swings open to expose an interior chamber for a powder-filled medication capsule to be dropped into, and the cover may then be closed. The medicinal extractor may have squeezable side depressors on each side for manually squeezing or holding the capsule in place horizontally. Once closed, the cover may be pushed down to compress two components of the medicinal extractor that are moveable with respect to each other. As the moveable components compress, the cover may press the capsule downward onto a hollow piercing element. The hollow piercing element may puncture the capsule to allow medication within the capsule to fall through the hollow piercing element and into a collection chamber or onto a surface below the medicinal extractor for collection.

20 Claims, 12 Drawing Sheets

CAPSULE OPENER AND EMPTIER

CROSS-REFERENCE TO RELATED APPLICATION

This patent application is a Continuation of U.S. patent application Ser. No. 13/328,481, entitled Capsule Opener and Emptier, and filed Dec. 16, 2011, the entirety of which is incorporated by reference herein in its entirety.

BACKGROUND OF INVENTION

1. Field of Invention

The present embodiments relate generally to capsules containing medication. In particular, the present embodiments relate to a device for opening or piercing such capsules, and extracting and collecting the medication therein.

2. Description of the Related Art

Conventional inhalers may be configured to puncture a capsule to allow the medication inside of the capsule to be inhaled. For instance, U.S. Pat. No. 6,705,313 to Niccolai; U.S. Pat. No. 5,263,475 to Alternatt et al.; U.S. Pat. No. 5,797,391 to Cook et al.; U.S. Pat. No. 7,832,399 to Ganem et al.; U.S. Pat. No. 3,518,992 to Altounyan et al.; and U.S. Pat. No. 7,284,553 to Hochrainer disclose typical inhalers.

More importantly, often times, with both over-the-counter medications and prescription medications, the need to open a capsule and utilize the powder inside that same capsule presents itself to a patient. The existing methodology to open capsules and collect the medication inside may involve the physical manipulation of the capsule and "opening" of the same by holding the capsule on opposite ends and twisting in opposite directions (on each side). Challenges to doing this type of physical manipulation of a capsule exist and include, but are not limited to: the patients' dexterity, disease states that patients' may have that would limit their ability to manipulate capsules (such as Parkinson's Disease or severe neuropathy), and/or variable sizes of capsules that make manipulation of the same too difficult. Conventional capsule opening techniques may have other drawbacks as well.

SUMMARY OF THE INVENTION

The present embodiments are directed toward a medicinal extractor, such as a capsule opener and emptier. In general, the medicinal extractor may efficiently open and then empty pharmaceutical capsules of variable sizes. The medicinal extractor may be in the shape of an upright rectangular box having a cover that swings or rotates open to expose an interior chamber for a powder-filled medication capsule to be dropped into, and then the cover may be closed. The medicinal extractor may have squeeze depressors on each side for a user to squeeze and hold the capsule in place horizontally (or in a first direction). Simultaneously, the closed cover may then be pushed vertically downward (or in a second direction approximately perpendicular to the first direction) to compress two or more components of the medicinal extractor, which are moveable with respect to each other, toward one another. The movable components may include a bottom piece and a middle piece. As the moveable components compress, the cover or an associated component of the medicinal extractor may press the capsule downward toward a hollow piercing element having a sharp edge. The piercing element may puncture the bottom of the capsule to allow the granular or powder contents within the capsule to fall through the hollow piercing blade and into a collection chamber or onto a surface below the medicinal extractor for subsequent collection.

In one aspect, a medicinal extractor for removing medication from capsules may be provided. The medicinal extractor may include an exterior; an interior chamber; and two side depressors. The two side depressors may be configured to squeeze a capsule from opposing sides to maintain the capsule horizontally stable within the interior chamber. The medicinal extractor may include a piercing element having a sharp or cutting edge and a hollow interior, and be located at or in the vicinity of a bottom of the interior chamber. The medicinal extractor may include a cover configured such that when pressure is manually exerted on the cover and/or a bottom piece of the medicinal extractor, the cover or an associated component of the medicinal extractor presses the capsule in the interior chamber downward and into the piercing element. As a result, the capsule may be pierced and medication within the capsule may gravity flow and/or be manually tapped into and/or through the hollow interior of the piercing element for collection.

In another aspect, a medicinal extractor for removing medication from capsules may be provided. The medicinal extractor may include a housing having at least a bottom piece and a middle piece. The bottom piece and the middle piece may be interconnected via at least one internal spring and be compressible or vertically movable with respect to one another. The medicinal extractor may include an interior chamber centrally located within the housing. The interior chamber may be defined, at least in part, by a portion of the middle piece. The medicinal extractor may include left and right manually operated side depressors. The side depressors may be configured to squeeze a capsule within the interior chamber in a first direction to maintain the capsule horizontally stable within the interior chamber. The medicinal extractor may include a piercing element having a sharp or cutting edge on top and a hollow interior. The piercing element may be centrally located with respect to the vertical axis of both the bottom piece and the middle piece. The medicinal extractor may include a cover, wherein manual pressure exerted on the cover and/or the bottom piece in a second direction forces the middle piece to move toward the bottom piece, which in turn moves the capsule in the interior chamber toward and into the piercing element to allow the capsule to be pierced and medication within the capsule to be collected.

In another aspect, a method of extracting medication from a capsule may be provided. The method may include placing a capsule in an internal chamber of a medicinal extractor; exerting a horizontal force on side depressors of the medicinal extractor to hold the capsule horizontally stable within the internal chamber; exerting a vertical force on a cover and/or a bottom piece of the medicinal extractor to move the capsule downward within the medicinal extractor and into a piercing element to pierce the capsule and allow the medication within the capsule to flow out of the capsule and be collected. When the vertical force is exerted on the cover and/or the bottom piece, the bottom piece of the medicinal extractor may move vertically with respect to a middle piece of the medicinal extractor, or otherwise toward the middle piece, to facilitate the piercing element puncturing the capsule.

The present invention is defined by the following claims. Nothing in this section should be taken as a limitation on those claims. Further aspects and advantages of the invention are discussed below in conjunction with the preferred embodiments and may be later claimed independently or in combination.

DESCRIPTION OF THE DRAWINGS

The present embodiments will become more fully understood from the detailed description given herein below and the accompanying drawings which are given by way of illustration only, and are not limitative of the present invention, and wherein.

DETAILED DESCRIPTION OF THE DRAWINGS

Figure 1A:
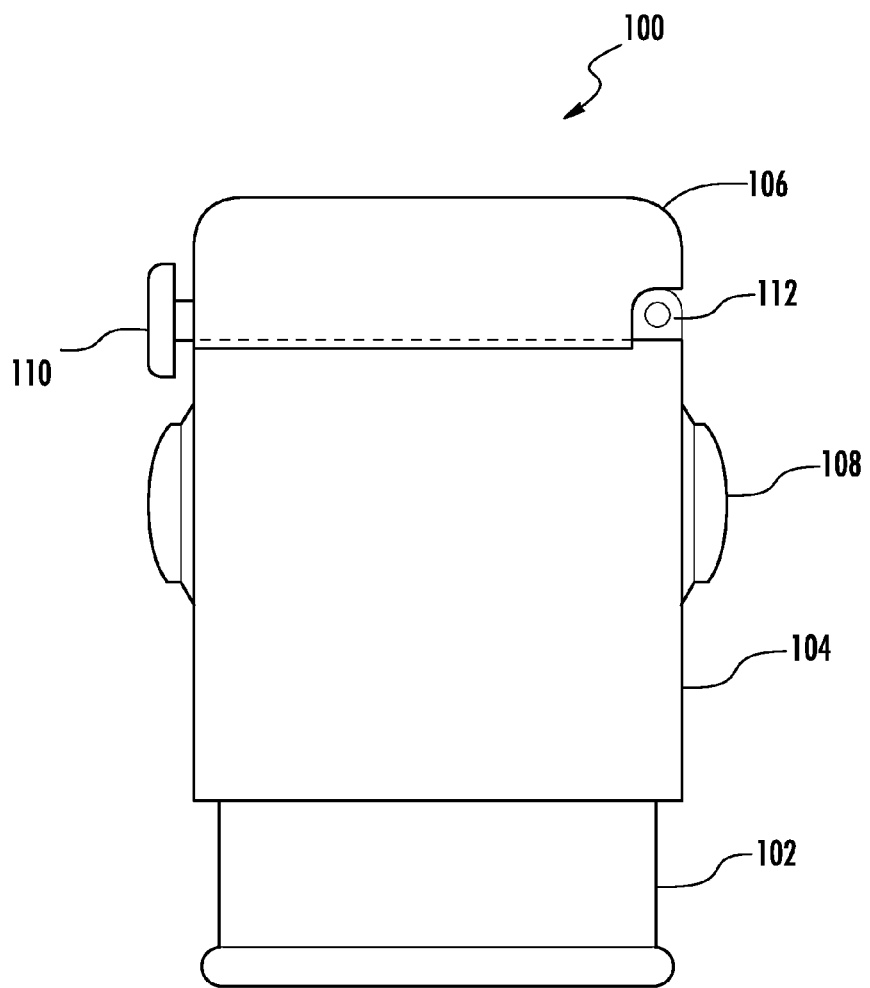
FIGS. 1A-1F illustrate exterior views of an exemplary medicinal extractor.

The present embodiments relate to a medicinal extractor. In general, the device may efficiently open and then empty pharmaceutical capsules of variable sizes. The medicinal extractor may allow a patient to simply drop a capsule into a hole within the medicinal extractor, squeeze depressors on the side of the medicinal extractor to hold the capsule in place while gently pushing down on the extractor which will pierce the capsule at the bottom of the capsule. After that is done, the patient may simply tap the entire device on a flat service where the powder inside the penetrated capsule will drop down through the hollow piercing device and into a reservoir or onto a surface that will collect the powder.

In one aspect, a medicinal extractor for removing medication from capsules may be provided. The medicinal extractor may include an exterior casing; an interior chamber; two side depressors configured to squeeze a capsule from opposing sides to maintain the capsule horizontally or otherwise stable within the interior chamber; and a piercing element having a sharp top and a hollow interior located at or in the vicinity of a bottom of the chamber. The medicinal extractor may include a cover configured such that when pressure is manually exerted on the cover, the cover or an associated component, such as a flap or ledge, presses the capsule in the interior chamber downward within the medicinal extractor and into the piercing element to allow the capsule to be pierced. Subsequently, medication within the capsule may run into and/or through the hollow interior of the piercing element for collection.

The two side depressors may comprise left and right side depressors. The left and right side depressors may be generally T-shaped, made of compressible material, such as rubber, and configured to move horizontally inward toward the interior chamber. The cover may be a rotatable cover with a depressible opening latch.

The medicinal extractor may comprise a bottom piece and a middle piece. The bottom piece and a lower portion of the middle piece may be interconnected via one or more internal springs, such as a left internal spring and a right internal spring. The bottom piece may have tapered edges in the vicinity of the top of the bottom piece that snap into ledges on the bottom of the middle piece to facilitate movement between the bottom piece and the middle piece during use. The bottom piece and the middle piece may be compressible and/or vertically movable with respect to one another when a force is manually exerted on the cover and/or bottom piece of the medicinal extractor and overcomes the resistive force of the internal springs.

In another aspect, a medicinal extractor for removing medication from capsules may be provided. The medicinal extractor may include a housing comprising at least a bottom piece and a middle piece. The bottom piece and the middle piece may be interconnected via at least one internal spring and be compressible and/or vertically movable with respect to one another. The medicinal extractor may include a vertical and interior chamber centrally located within the housing, the interior chamber being defined in part by a central portion of the middle piece. The medicinal extractor may include left and right manually operated side depressors configured to squeeze a capsule within the interior chamber to maintain the capsule horizontally or otherwise stable within the interior chamber, and a piercing element having a cutting edge on top and a hollow interior. The piercing element may be centrally located within both the bottom piece and a lower portion of the middle piece. The medicinal extractor may include a cover, wherein manual pressure exerted on the cover and/or the bottom piece forces the middle piece to move toward or downward with respect to the bottom piece, which in turn moves the capsule in the interior chamber downward and into the piercing element. As a result, the capsule may be pierced and medication within the capsule may flow into a collection chamber within or below the medicinal extractor, or onto a flat surface or device below the medicinal extractor for collection.

The medicinal extractor may further comprise one or more internal springs, such as a left internal spring and a right internal spring, that facilitate vertical or other movement between the bottom piece and the middle piece, such as first toward and then away from each other during use. Also, the left and right manually operated side depressors may comprise a portion of the exterior of the medicinal extractor and be located above the bottom piece and/or the lower portion of the middle piece. The left and right side depressors may be generally T-shaped, made of compressible material, and configured to move horizontally inward toward the interior chamber.

In another embodiment, a method for extracting medication from a capsule may be provided. The method may include depressing an opening latch and rotating open a rotatable cover of the medicinal extractor; placing a capsule in an internal chamber of a medicinal extractor; exerting a horizontal force on side depressors of the medicinal extractor to hold the capsule horizontally stable within the internal chamber; exerting a vertical or other compressing force on a cover and/or a bottom piece of the medicinal extractor to move the capsule within the interior chamber downward and into a piercing element to pierce the capsule and allow the medication within the capsule to fall into a collection chamber or otherwise be collected. As compressing force is exerted on the cover and/or the bottom piece, the bottom piece of the medicinal extractor may move toward, such as vertically with respect to, a middle piece of the medicinal extractor to compress the medicinal extractor and to facilitate the piercing of the capsule by the piercing element.

The method may include squeezing side depressors that may be generally T-shaped and/or made of rubber. The side depressors may be manually movable in a first direction, such as horizontally when the medicinal extractor is resting in its normal upright position. The side depressors may be configured to work in conjunction with other movable pieces of the medicinal extractor. For instance, the medicinal extractor may have movable components that move with respect to each other in a second direction that is different from the first direction. The first direction may be approximately perpendicular to the second direction—for example, the second direction may be a vertical direction when the medicinal extractor is resting in its normal upright position. In one embodiment, the medicinal extractor may include a bottom piece and a middle piece that first move toward and then away from each other during use. The method may include snapping tapered edges of the bottom piece into bottom edges located at or in the vicinity of the bottom of the middle piece as part of assembling the medicinal extractor.

The method may also involve using a medical extractor that may have manually operated side depressors that hold the capsule stable in one direction, such as horizontally stable, within an interior chamber. The medicinal extractor may simultaneously allow a force in a second direction to be exerted on the capsule, such as a downward or vertical force. As a result, the capsule may be moved toward a piercing element and then the medication within the capsule may be collected.

The method may also involve using a medicinal extractor that may be in the shape of an upright rectangular-shaped exterior or casing, and having a cover or top that swings open to expose an interior chamber for a powder-filled medication capsule to be dropped into. After which, the cover may be closed. The casing may have squeezable side depressors on each side for the user to squeeze and hold the capsule in place.

I. Exemplary Medicinal Extractor

Figure 1B:
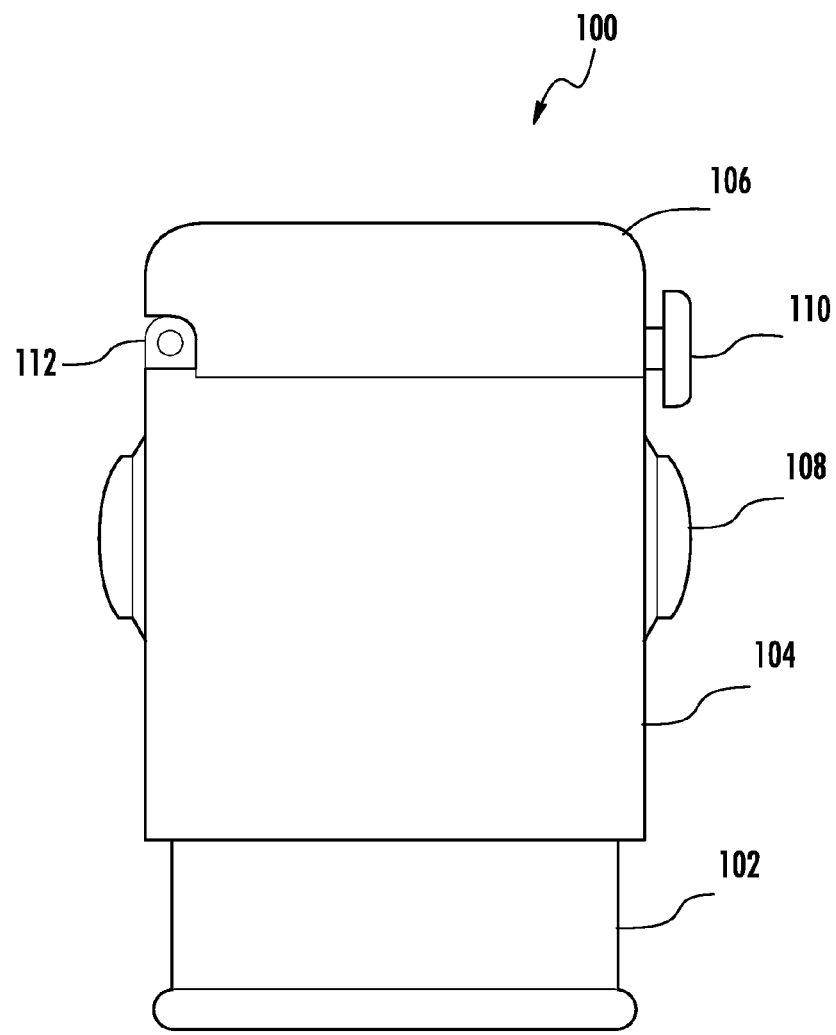

FIGS. 1A-1F illustrate exterior views of an exemplary medicinal extractor. FIG. 1A depicts an exemplary front view, and FIG. 1B depicts an exemplary back view of the medicinal extractor 100. The medicinal extractor 100 may include a bottom piece 102, a middle piece 104, a cover 106, side depressors 108, an opening latch 110, and at least one hinge 112. The medicinal extractor 100 may include additional, fewer, or alternative components.

During operation, an operator may depress the opening latch 110 and lift up on the cover 106 such that the cover 106 rotates about the hinge 112 and opens. An interior chamber or channel within the medicinal extractor 100 may be exposed, and a capsule (of differing sizes) may be placed in the interior chamber. The cover 106 may be rotated shut and the opening latch 110 may snap back into a closed position. The interior chamber may have a diameter that is larger than the capsule, and may accommodate capsules of various sizes and diameters. A user may exert force on the side depressors 108 in a first direction, such as inward and/or horizontally, to hold the capsule stable and prevent the capsule from moving within interior chamber.

The bottom piece 102 and the middle piece 104/cover 106 assembly may be moveable with respect to each other. When pushing on the side depressors 108 to hold the capsule stable in the first direction, the user may exert a compressing force onto the medicinal extractor 100 in a second direction. For instance, the user may push down on the cover 106, which may move the middle piece 104 that holds the capsule toward and/or downward with respect to the bottom piece 102. An internal, hollow piercing element may be located within the medicinal extractor 100 that pierces the capsule as it is pushed downward. As a result, the medication in the capsule may gravity flow through the piercing element and into a collection chamber and/or out of the bottom piece 102 and onto a table or other flat surface for collection. The user may facilitate medication flowing out of the capsule by tapping the medicinal extractor, such as on either the cover 106 or the bottom piece 102.

Figure 1C:
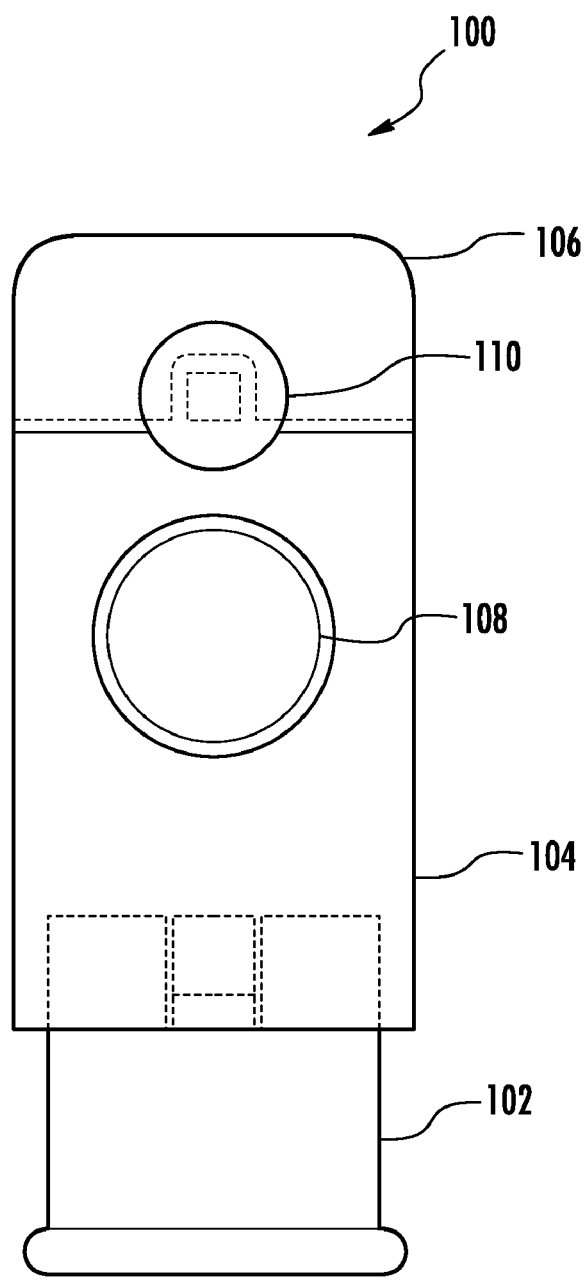

FIG. 1C depicts a left side view of the medicinal extractor 100. The side depressors 108 may enter the interior of the medicinal extractor 100 via a cavity, chamber, or channel in the middle piece 104. The opening latch 110 may enter the interior of the medicinal extractor 100 via a cavity, chamber, or channel in the cover 106. In one embodiment, the exterior button portion of the opening latch 110 may have a diameter of approximately 9.0 mm, and the exterior circular portion of the side depressors 108 may have a diameter of approximately 15.0 mm. Other dimensions may be used.

Figure 1D:
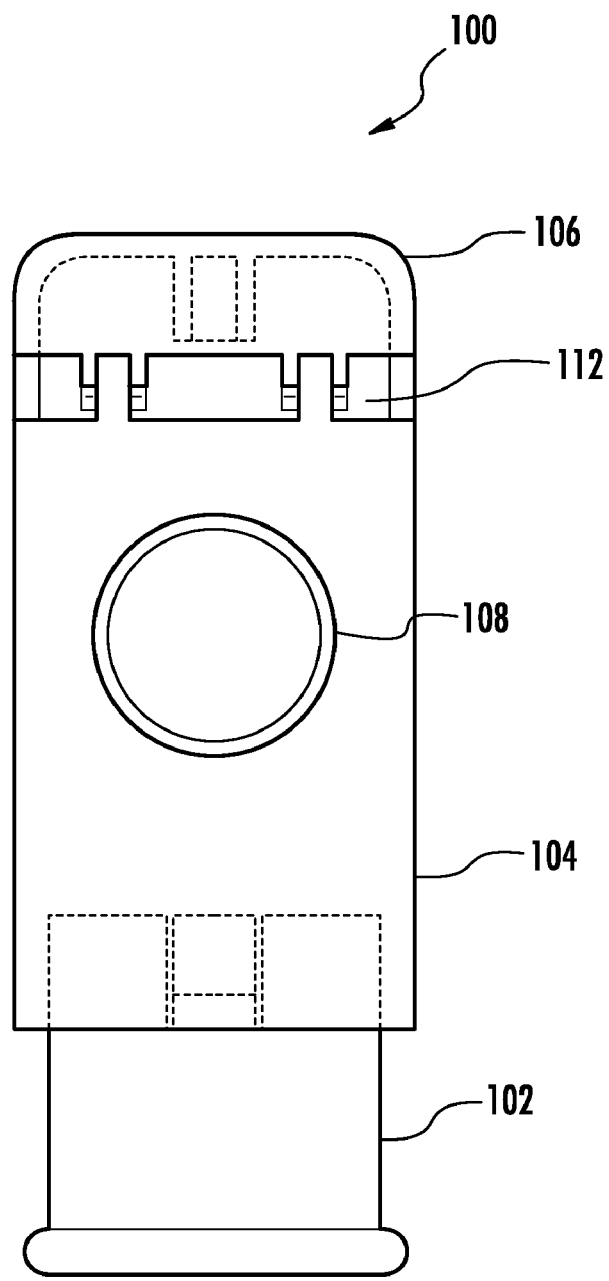

FIG. 1D depicts a right side view of the medicinal extractor 100. As shown, the cover 106 may be connected to the middle piece 104 via two hinges 112. In one embodiment, the cover 106 may be approximately 12.3 mm in height, and the hinges 112 may have longitudinal portions that extend downward from the cover 106 that may be approximately 1.0 mm in width and approximately 2.0 mm in length. With respect to FIG. 1D, the middle piece 104 may have a height of approximately 37.9 mm, a side width of approximately 24.7 mm, and upwardly extending hinge arms that are approximately 5.0 mm in length. With respect to FIG. 1A, the middle piece 104 may have a front width of approximately 40.0 mm. Other dimensions may be used.

Figure 1E:
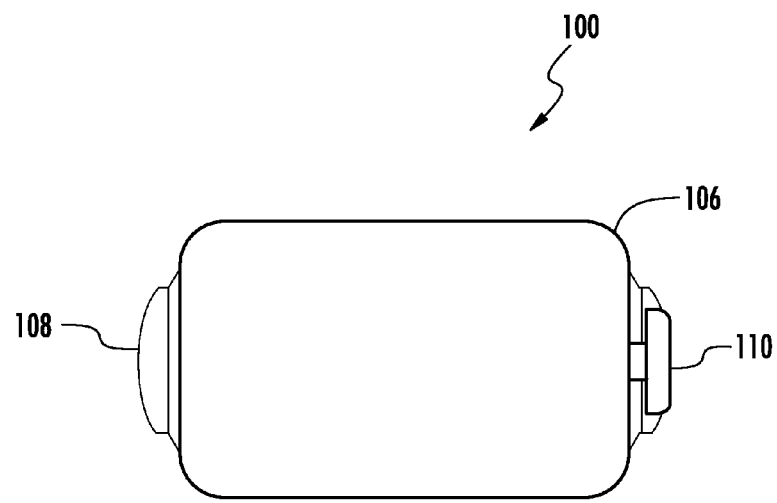

FIG. 1E depicts a top view of the medicinal extractor 100. As shown, the top of the cover 106 may be smooth and flat. In one embodiment, the cover 106, when viewed from above, may be approximately 40.0 mm in length, and approximately 24.7 mm in width. Other dimensions may be used.

Figure 1F:
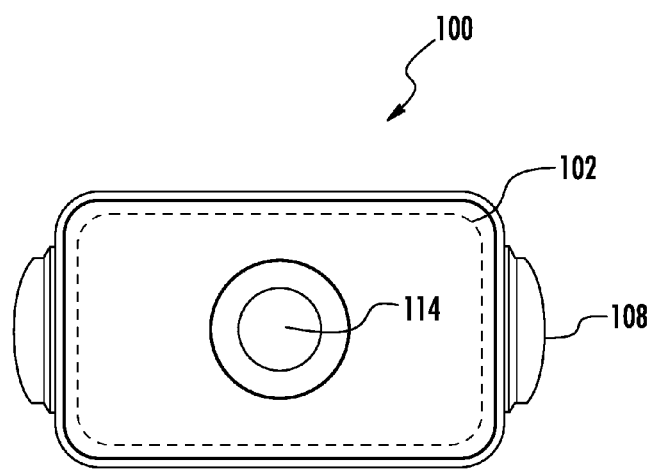

FIG. 1F depicts a bottom view of the medicinal extractor 100. As shown, the bottom piece 102 may include a centrally located chamber or channel 114. Within the central chamber 114 may reside a piercing element as discussed herein. The piercing element may be hollow to allow medication to fall through it and then out of the medicinal extractor 100 and onto a table or flat surface, or into a collection device thereon, such as a bowl. Alternatively, the piercing element or the central chamber 114 themselves may be configured to act as a collection device.

In one embodiment, when viewed from below, the bottom piece 102 may be approximately 38.8 mm in length at the base and approximately 23.5 mm in width. The bottom piece 102 may be approximately 22.3 in height. The central chamber 114 may have an interior radius of approximately 3.6 mm, and a larger radius of approximately 6.2 mm near, or in the vicinity of, the bottom of the bottom piece 102. Other dimensions may be used.

II. Exemplary Cross-Sectional View of the Medicinal Extractor

Figure 2:
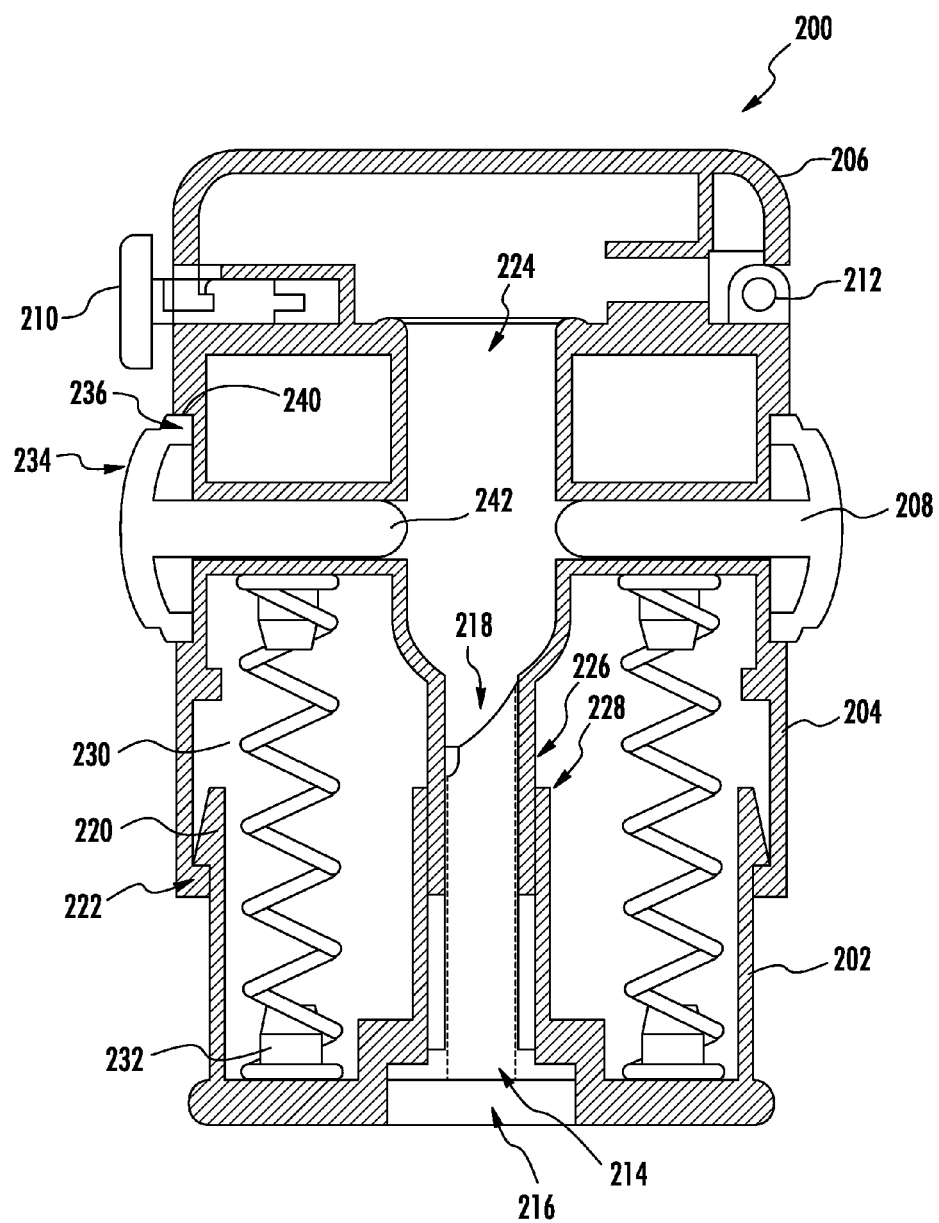
FIG. 2 illustrates an exemplary cross-sectional view of the medicinal extractor.

FIG. 2 depicts an exemplary cross-sectional view of the medicinal extractor 200. The medicinal extractor 200 may include a bottom piece 202, a middle piece 204, a cover 206, side depressors 208, an opening latch 210, one or more hinges 212, a piercing element 214, internal springs 230, and internal studs 232. The medicinal extractor 200 may include additional, fewer, or alternate components.

The bottom piece 202 may include outer arms having top tapered edges 220 for snap-in interconnection with the bottom ledges 222 on the lower portion of the middle piece 204. The bottom piece 202 may include a central chamber 216 in which the piercing element 214 may be located. The bottom piece 202 may include two or more bottom studs or pegs 232. The studs 232 may be interconnected with the internal springs 230.

The lower portion of the middle piece 204 may include bottom ledges 222 that snap over the tapered edges 220 of the bottom piece 202. The lower portion of the middle piece 204 may include upper studs or pegs 232. The studs 232 may be interconnected to the top of the internal springs 230. The interior of the middle piece 204 may define an interior chamber 224 that may hold capsules of different sizes. An interior portion of the middle piece 204 may be curved to facilitate holding a capsule horizontally in place in conjunction with the side depressors 208.

Each side depressor 208 may reside within a tubular and horizontal channel within the middle piece 204. The horizontal channel may support and/or surround the long portion 242 of the side depressors 208, such as via either clearance or interference fits. The middle piece 204 may have an outer corner edge 240 on its exterior for holding each side depressor 208 in place.

The side depressors 208 may be made from compressible materials, such as rubber. The side depressors 208 may be generally T-shaped with a curved outer surface. Force exerted on the outer surface of the side depressors 208 may move the long tubular portion 242 of the side depressors 208 inward toward a central chamber.

The T-shaped portion of the side depressors 208 may include a flexible end-piece 234. The flexible end-piece 234 may be curved or concave shaped to facilitate flexibility during use. The flexible end-piece 234 may include a jagged piece 236 that has surfaces configured to mate with the corner edge 240 of the middle piece 204 and to hold the side depressors 208 in place with respect to the middle piece 204.

The middle piece 204 may be interconnected with the cover 206, such as via the hinges 212 and opening latch 210. The cover 206 may be rotatable about the hinges 212. One side of the cover 206 may be rotatable mounted to the middle piece 204 and the other side may have an opening latch 210. The opening latch 210 may be a spring-loaded latch such that inward force may unlatch the cover 206 and allow the user to open the cover 206 and insert a capsule into the internal chamber 224. The cover 206 may also include one or more pieces of silicon or tubing that allow smooth rotation of the cover 206 with respect to the hinges 212.

The bottom piece 202 and middle piece 204 may be configured to move toward and then away from each other. The internal springs 230 may have ends supported by studs 232 on the bottom piece 202 and the middle piece 204. By pressing down on the cover 206, the internal springs 230 may be compressed, and the middle piece 204 may move downward with respect to the bottom piece 202. The outer arm with the tapered edge 220 and the inner arm 228 of the bottom piece 202 are configured to be primarily flat and straight, and to fit within corresponding arms on the middle piece 204, such as the outer arm with the lower ledge 222 and the inner arm 226. There may be clearance or interference fits between the corresponding arms, but preferably clearance fits to facilitate overcoming the resistive spring force during use and moving the middle piece 204 toward the bottom piece 202.

As the middle piece 204 is moved toward the bottom piece 202, the cover 206 or an associated component may press against and force the capsule in the interior chamber 224 into a sharp edge or blade 218 on the piercing element 214. The blade 218 may puncture the capsule. Then, after the manual downward force is removed, the internal springs 230 may move the middle piece 204 upward and away from the bottom piece 202 and the blade 218.

During use, the sharp edge or blade 218 may pierce the outer casing of a capsule and allow medication to flow from the capsule either immediately upon puncture or after the internal springs 230 separate the middle piece 204 from the bottom piece 202, and as a result, separate the capsule from the sharp edge 218 of the piercing element 214. The medication may gravity flow from the capsule or a user may tap the medicinal extractor 200 to cause the medication to exit the capsule. The medication may flow through the hollow piercing element 214 and out of the medicinal extractor 200 for subsequent collection and/or be collected in a container located at the bottom of the medicinal extractor 200.

Also with respect to FIG. 2, each internal spring 230 may be a constant pitch compression spring, and may have a spring index of approximately 5.5, a pitch of approximately 5.4 mm, an outside diameter of approximately 6.5 mm, a diameter of approximately 5.5 mm, an inside diameter of approximately 4.5 mm, a wire diameter of approximately 1.0 mm, and a free length of approximately 33.6 mm. The internal springs 212 may be made of metal or other materials. Additionally, the opening latch 210 may be approximately 12.0 mm in length and have a staggered diameter of approximately 1.2 mm for the tip, approximately 2.9 mm for the latching portion, and approximately 9.0 mm for the button portion. Other dimensions may be used.

III. Exemplary Cross-Section of the Bottom Piece

The exterior and interior vertical surfaces or arms of the middle piece 204 may be configured to have either interference or clearance fits with respect to corresponding exterior and interior surfaces or arms of the bottom piece 214. Preferably, there are clearance fits between the corresponding exterior and interior vertical surfaces of the middle piece 204 and the bottom piece 202 to facilitate ease of manually compressing the internal springs 230 and moving the middle piece 204, and thus moving a capsule within the internal chamber 224, downward and onto the piercing element 214.

Figure 3:
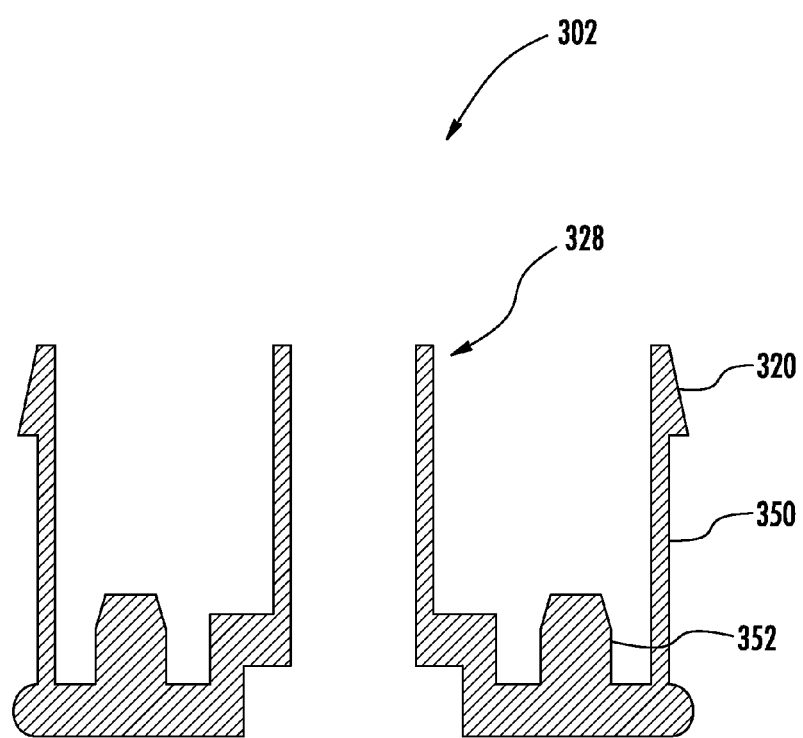
FIG. 3 illustrates an exemplary cross-sectional view of the bottom piece of the medicinal extractor.

FIG. 3 depicts an exemplary cross-sectional view of the bottom piece 302. The bottom piece may have a height of approximately 22.3 mm. The distance between the exterior and interior upwardly extending arms 328, 350 of the bottom piece 302 may be approximately 12.3 mm. Each arm 328, 350 may be approximately 1.0 mm wide. The distance between the two interior upwardly extending arms 328 may be approximately 7.2 mm at the top of the bottom piece 302, and approximately 12.4 mm at the bottom of the bottom piece 302.

The upwardly extending interior arms 328 may be approximately 15.3 mm in vertical length at the top of the bottom piece, followed by a L-shaped jag that may be approximately 3.0 mm in vertical length, which in turn may be followed by a bottom portion that is approximately 4.0 mm in vertical thickness. The bottom portion of the bottom piece 302 may be approximately 38.8 mm in horizontal width, and the top portion of the bottom piece 302 may be approximately 35.8 mm in horizontal width.

The tapered edge 320 of the bottom piece 302 may be approximately 1.0 mm in width at the top, approximately 2.0 mm in width at the bottom of the taper, and the taper may run approximately 5.0 mm in length.

The bottom studs 352 of the bottom piece 302 may be approximately 3.0 mm in width at the top of the studs 352, expanding to approximately 4.0 mm in width at the bottom of the studs 352, and be approximately 3.5 mm in height. Other dimensions for the vertical arms, tapered edge, bottom studs and other bottom piece components discussed above may be used.

IV. Exemplary Cross-Section of Middle Piece

Figure 4A:
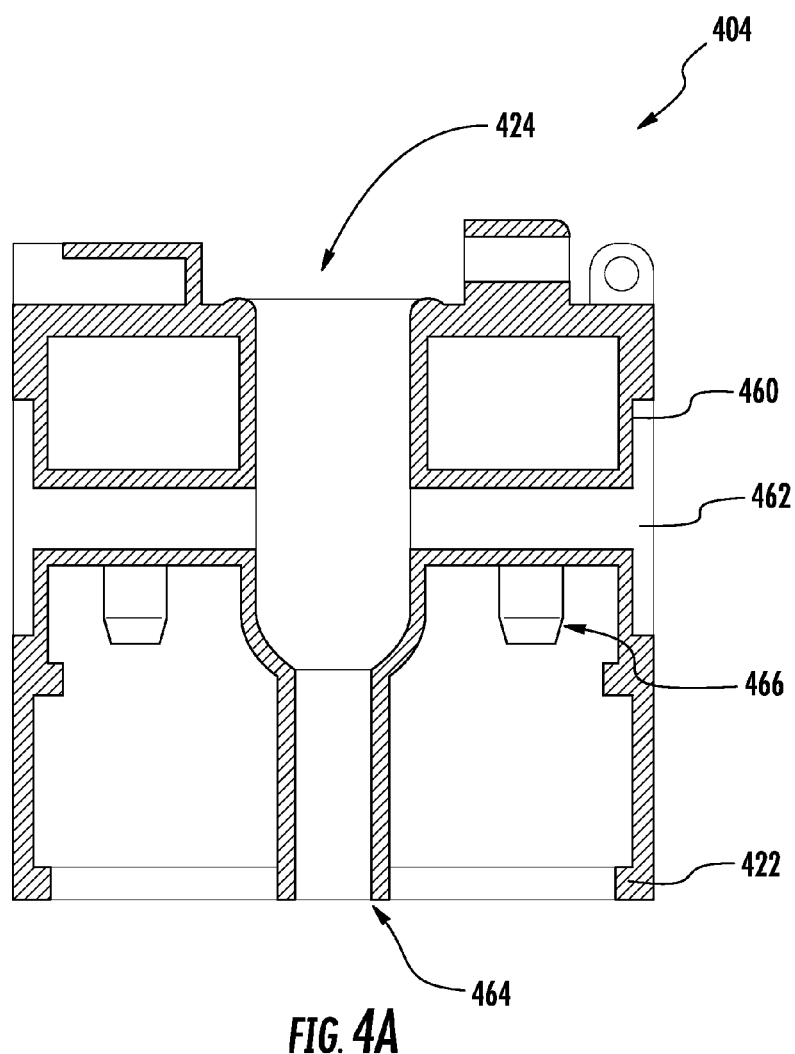
FIG. 4A illustrates an exemplary cross-sectional view of the middle piece of the medicinal extractor.

FIG. 4A illustrates an exemplary cross-sectional view of the middle piece 404 of the medicinal extractor. The middle piece 404 may define an interior chamber 424 configured to hold capsules of various sizes. The middle piece 404 may include an interior arm 464 and an exterior arm that includes a lower ledge 422. The interior arm 464 may be configured to slide over the top of a corresponding arm of the bottom piece, while the lower ledge 422 may be configured to snap over a tapered edge on the bottom piece.

The middle piece 404 may include one or more studs 466. The studs 466 may be interconnected with internal springs that facilitate movement of the middle piece 404 toward and away from the bottom piece.

The middle piece 404 may include an interior, horizontal channel 462 for housing a long, tubular portion of a T-shaped side depressor. The middle piece 404 may include one or more surfaces 460 configured to hold the side depressor in place with respect to the middle piece 404.

In one embodiment, the middle piece 404 may have a width of approximately 40.0 mm and a height of approximately 43.4 mm. Other dimensions may be used.

Figure 4B:
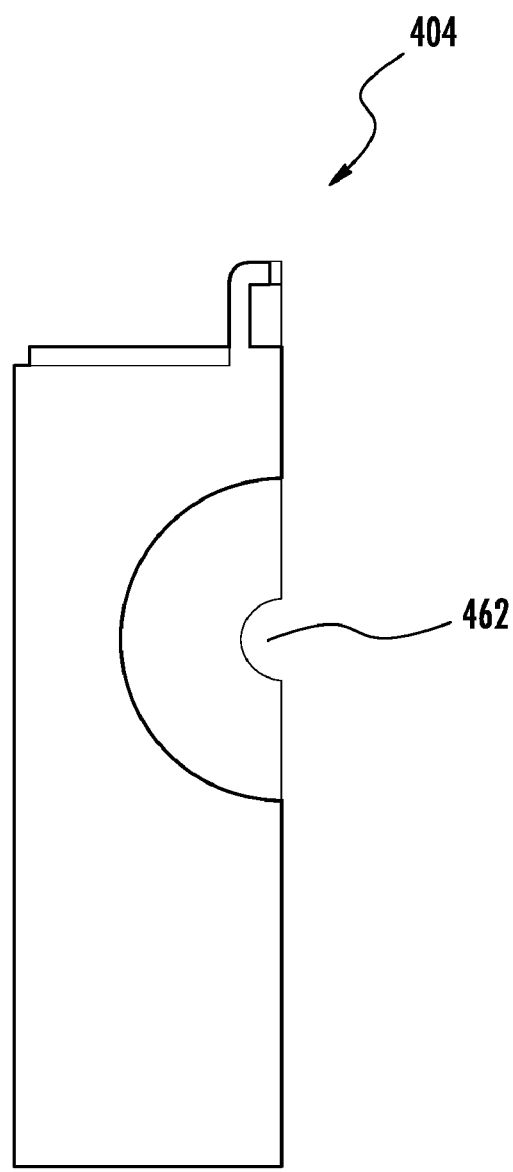
FIG. 4B illustrates an exemplary side view of one half of the middle piece of the medicinal extractor.

The middle piece 404 may include a left and a right half that are snapped or glued together, or otherwise interconnected to make the full middle piece. FIG. 4B illustrates an exemplary side view of one half of the middle piece 404 of the medicinal extractor. As shown, the middle piece 404 may include an interior, tubular channel 462 for housing a side depressor.

V. Exemplary Side Depressor

Figure 5:
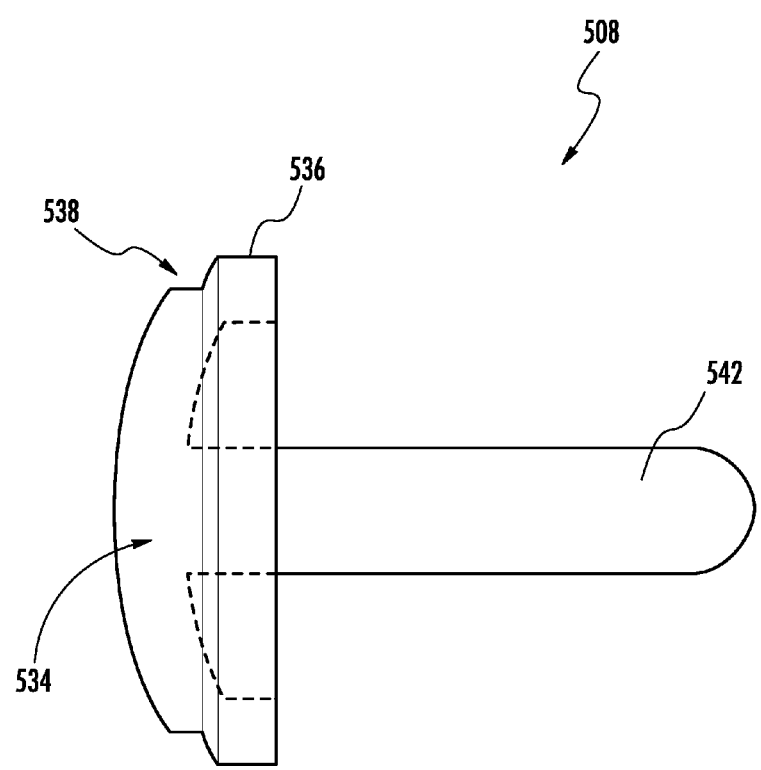
FIG. 5 illustrates an exemplary side depressor of the medicinal extractor.

FIG. 5 illustrates an exemplary side depressor 508 of the medicinal extractor. The side-depressor 508 may have a flexible, curved T-shaped portion 534 that is made of resilient materials and facilitates pushing in the side depressors 508 to squeeze a capsule within the middle piece. The side depressor 508 may include a long portion 542 that resides in a horizontal channel within the middle piece. The long portion 542 may be generally tubular in shape, and movable horizontally. The side depressor may include additional, fewer, or alternative components.

The total length of the side depressor 508 may be approximately 18.7 mm. The long portion 542 may have a diameter of approximately 3.8 mm, and a length of approximately 16.7 mm. The T-shaped portion 534 may have a double domed exterior. The T-shaped portion 534 may have an outer diameter of approximately 15.0 mm for the outermost dome 536, and a diameter of approximately 13.0 mm for the inner dome 538. The T-shaped portion 534 may have a width or thickness of approximately 4.5 mm. Other dimensions may be used.

VI. Exemplary Piercing Element

Figure 6:
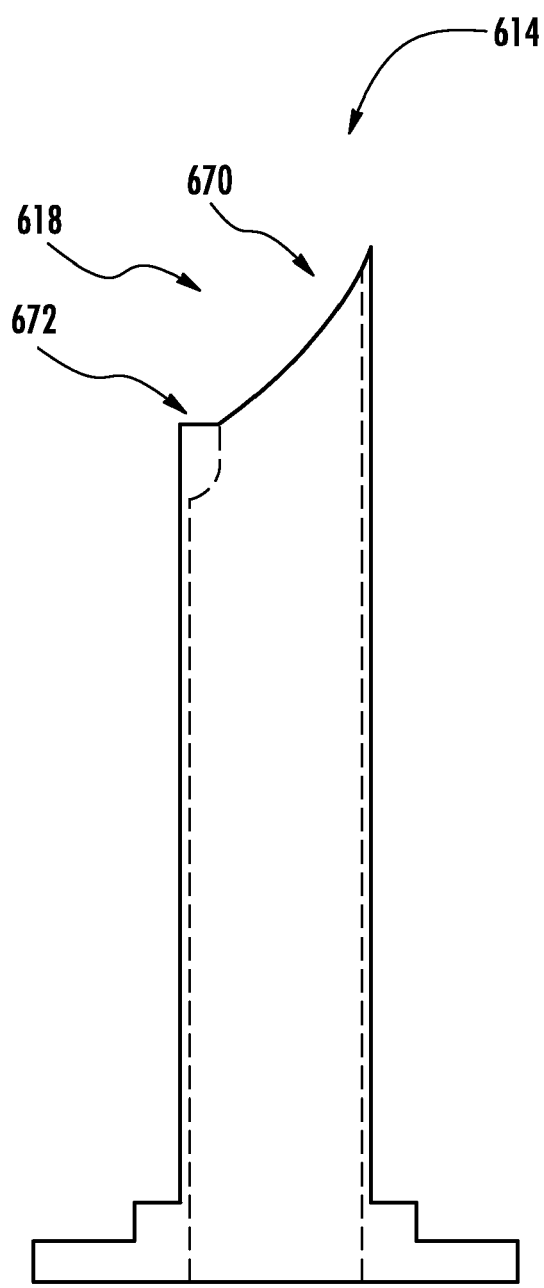
FIG. 6 illustrates an exemplary piercing element of the medicinal extractor.

FIG. 6 illustrates an exemplary piercing element 614 of the medicinal extractor. The piercing element 614 may have a hollow interior and a sharp top or cutting portion 618. The sharp top 618 may have a tapered edge that runs into a horizontal portion. The piercing element 614 may have additional, fewer, or alternate components.

In one embodiment, the sharp top 618 may include a beveled sharpened edge 670 and a flat edge 672. The flat edge 672 may be approximately 1.0 mm in length. The piercing element 614 may have a diameter of approximately 4.8 mm, except for at the very bottom, the diameter of the piercing element 614 may expand to approximately 12.4 mm. The piercing element 614 may be approximately 26.5 mm in height. Other dimensions may be used.

VII. Exemplary Method

In one aspect, a method of extracting medication from a capsule may be provided. The method may include placing a capsule in an internal chamber of a medicinal extractor; exerting a force in a first direction, such as horizontally, on side depressors of the medicinal extractor to hold the capsule horizontal stable within the internal chamber; exerting another force in a second direction, such as vertically or perpendicular to the first force, on a cover and/or a bottom piece of the medicinal extractor to move the capsule in the interior chamber (such as downward) and into a piercing element to pierce the capsule and allow the medication within the capsule to be collected. When the vertical force is exerted on the cover and/or the bottom piece, the bottom piece of the medicinal extractor may move vertically with respect to a middle piece of the medicinal extractor to facilitate the piercing element puncturing the capsule.

Figure 7:
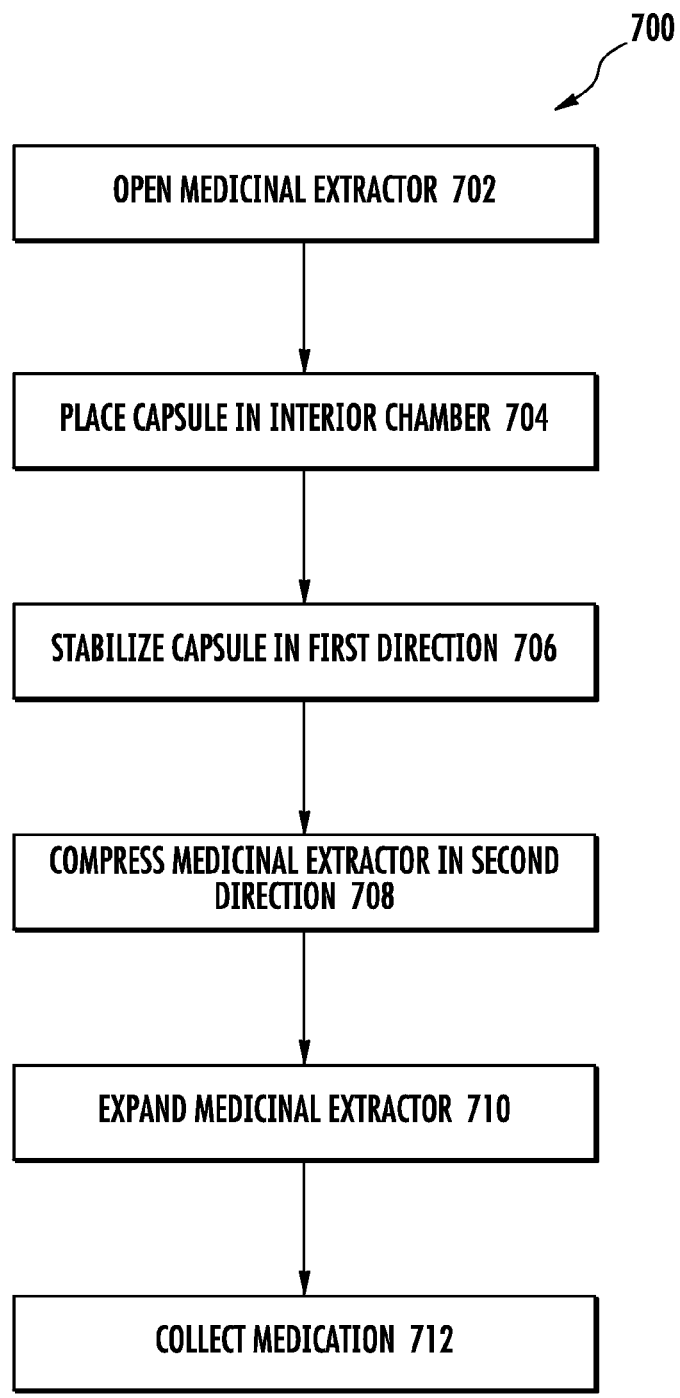
FIG. 7 illustrates an exemplary method of extracting medication from a capsule.

FIG. 7 illustrates an exemplary method of extracting medication from a capsule 700. The method 700 may include opening the medicinal extractor 702, placing a capsule within the medicinal extractor 704, stabilizing the capsule 706, compressing the medicinal extractor 708, expanding the medicinal extractor 710, and collecting the medication 712. The method may include additional, alternate, or fewer actions.

The method 700 may include opening the medicinal extractor 702. The method may include pushing in an opening latch on a cover and then rotating the cover open.

The method 700 may include placing a capsule within the medicinal extractor 704. After the cover is rotated open, a capsule may be placed within a central chamber or area within the medicinal extractor. After which, the cover may then be rotated shut, enclosing the capsule within the central chamber. In the chamber, the capsule may be situated directly above a piercing device having a beveled sharpened edge and a flat edge.

The method 700 may including stabilizing the capsule 706 within the interior chamber. The user may squeeze side depressors to move the side depressors inward. The tips of the side depressors may come in contact with the capsule and hold it steady in a first direction, such as horizontally steady. The capsule may be held steady in other directions as well.

The method 700 may include compressing the medicinal extractor 708. The medicinal extractor may be compressed in a second direction that is different from the first direction. In one embodiment, the second direction may be a generally vertical direction, and the first direction may be a generally horizontal direction such that the second direction is offset from the first direction by approximately 90 degrees. Other second directions may be used.

In one embodiment, the method may involve exerting force on the cover of the medicinal extractor to overcome resistive force of internal springs, and move a middle piece of the medicinal extractor toward a bottom piece, which may also move the capsule in the interior chamber toward the piercing device. After the capsule is moved enough within the medicinal extractor, the capsule may be punctured by the piercing device.

The method 700 may include expanding the medicinal extractor 710. After the capsule is punctured, a user may stop exerting force on the cover of the medicinal extractor. The internal springs may then cause the middle piece and the bottom piece to move away from each, returning to their resting or normal positions. As a result, the tip of the piercing device may be automatically removed from inside of the capsule by the internal springs, opening a hole in the exterior of the capsule.

The method 700 may include collecting the medication 712. After the capsule is punctured, or after the internal springs remove the sharpened edge of the piercing device from the capsule and expose the interior of the capsule, the medicine inside of the capsule may run into the hollow interior of the piercing device for collection in a reservoir. In other words, the puncture(s) at the bottom of the capsule may allow the granular or powder contents to fall through the hollow piercing blade and into a collection chamber or onto a surface below the medicinal extractor.

While several arrangements of the invention have been described, it will be understood that it is capable of still further modifications and this application is intended to cover any variations, uses, or adaptations of the invention, following in general the principles of the invention and including such departures from the present disclosure as to come within knowledge or customary practice in the art to which the invention pertains, and as may be applied to the essential features hereinbefore set forth and falling within the scope of the invention or the limits of the appended claims. It should be understood that many changes and modifications may be made without departing from the scope of the invention. The description and illustrations are by way of example only. Many more embodiments and implementations are possible within the scope of this invention and will be apparent to those of ordinary skill in the art. The various embodiments are not limited to the described environments and have a wide variety of applications.

It is intended in the appended claims to cover all such changes and modifications which fall within the true spirit and scope of the invention. Therefore, the invention is not limited to the specific details, representative embodiments, and illustrated examples in this description. Accordingly, the invention is not to be restricted except in light as necessitated by the accompanying claims and their equivalents.

What is claimed is:

1. A medicinal extractor for removing medication from capsules, the medicinal extractor comprising:
   an exterior;
   an interior chamber;
   two side depressors configured to squeeze a capsule from opposing sides to maintain the capsule horizontally stable within the interior chamber;
   a piercing element having a sharp edge and a hollow interior, the piercing element being located at a bottom of the interior chamber; and
   a cover configured such that when pressure is manually exerted on the cover, the cover or an associated component of the medicinal extractor presses the capsule within the interior chamber downward and into the piercing element allowing the capsule to be pierced and medication within the capsule to gravity flow and/or be manually tapped into the hollow interior of the piercing element for collection.

2. The medicinal extractor of claim 1, wherein the two side depressors comprise left and right side depressors, the left and right side depressors being generally T-shaped, made of compressible material, and configured to move horizontally inward toward the interior chamber.

3. The medicinal extractor of claim 1, wherein the two side depressors comprise left and right side depressors that are made of rubber and movable in the horizontal direction with respect to the medicinal extractor.

4. The medicinal extractor of claim 1, wherein the medicinal extractor further comprises a bottom piece and a middle piece that are interconnected via at least one internal spring, the bottom piece and the middle piece being movable toward one another when a force is manually exerted on the cover and/or the bottom piece that overcomes the resistive force of the at least one internal spring.

5. The medicinal extractor of claim 1, wherein the medicinal extractor further comprises a rotatable cover with a depressible opening latch.

6. The medicinal extractor of claim 1, wherein the medicinal extractor further comprises a bottom piece and a middle piece, the bottom piece and the middle piece being movable toward one another to allow a capsule in the interior chamber to be pierced by the sharp edge of the piercing element.

7. The medicinal extractor of claim 6, wherein the medicinal extractor further comprises internal springs that are attached to studs on the bottom piece and the middle piece.

8. The medicinal extractor of claim 7, wherein the bottom piece has tapered edges that snap into corresponding ledges on a bottom portion of the middle piece to facilitate movement between the bottom piece and the middle piece during use.

9. A medicinal extractor for removing medication from capsules, the medicinal extractor comprising:
   a housing comprising at least a bottom piece and a middle piece, the bottom piece and the middle piece being interconnected via at least one internal spring and being vertically movable with respect to one another;
   an interior chamber centrally located within the housing, the interior chamber being defined in part by an internal portion of the middle piece;
   left and right manually operated side depressors configured to squeeze a capsule within the interior chamber in a first direction to maintain the capsule stable within the interior chamber;
   a piercing element having a cutting edge on top and a hollow interior, the piercing element being centrally located with respect to a vertical axis of both the bottom piece and the middle piece; and
   a cover, wherein manual pressure exerted on the cover and/or the bottom piece in a second direction forces the middle piece to move toward the bottom piece, which in turn moves the capsule in the interior chamber toward and into the piercing element to allow the capsule to be pierced and medication within the capsule to be collected.

10. The medicinal extractor of claim 9, wherein the first direction is approximately horizontal, and the second direction is approximately vertical such that the first direction is offset from the second direction by approximately 90 degrees.

11. The medicinal extractor of claim 9, wherein the left and right manually operated side depressors comprise a portion of the exterior and are located above the bottom piece vertically and are supported by a tubular channel in the middle piece.

12. The medicinal extractor of claim 9, wherein the left and right side depressors are generally T-shaped, made of compressible material, and configured to move horizontally inward toward the interior chamber.

13. The medicinal extractor of claim 9, wherein the left and right side depressors are made of rubber and movable in the horizontal direction.

14. The medicinal extractor of claim 9, wherein the medicinal extractor further comprises a rotatable cover with a depressible opening latch.

15. The medicinal extractor of claim 9, wherein the medicinal extractor further comprises a left internal spring and a right internal spring that facilitate compressible movement between the bottom piece and the middle piece.

16. The medicinal extractor of claim 15, wherein the bottom piece has tapered edges that snap into corresponding ledges on a bottom portion of the middle piece.

17. A method for extracting medication from a capsule, the method comprising:
   placing a capsule in an internal chamber of a medicinal extractor;

exerting a horizontal force on side depressors of the medicinal extractor to hold the capsule horizontally stable within the internal chamber; and exerting a vertical force on a cover and/or a bottom piece of the medicinal extractor to move the capsule in the interior chamber downward and into a piercing element to pierce the capsule and allow the medication within the capsule to flow out of the capsule and be collected.

18. The method of claim 17, wherein, when the vertical force is exerted on the cover and/or the bottom piece of the medicinal extractor, a middle piece of the medicinal extractor in which the capsule is situated is moved toward the bottom piece to facilitate the piercing element piercing the capsule.

19. The method of claim 18, wherein the side depressors are made of rubber and generally T-shaped.

20. The method of claim 19, wherein the bottom piece has tapered edges that snap into a bottom portion of the middle piece.

* * * * *